(12) United States Patent
Zhu et al.

(10) Patent No.: US 11,944,470 B2
(45) Date of Patent: Apr. 2, 2024

(54) METHOD AND DEVICE FOR SAMPLING A PULSE SIGNAL, AND COMPUTER PROGRAM MEDIUM

(71) Applicant: Raycan Technology Co., Ltd. (Suzhou), Suzhou (CN)

(72) Inventors: Kezhang Zhu, Suzhou (CN); Qingguo Xie, Suzhou (CN); Pingping Dai, Suzhou (CN); Hao Wang, Suzhou (CN); Junhua Mei, Suzhou (CN); Yuming Su, Suzhou (CN)

(73) Assignee: Raycan Technology Co., Ltd. (Suzhou), Suzhou (CN)

( * ) Notice: Subject to any disclaimer, the term of this patent is extended or adjusted under 35 U.S.C. 154(b) by 624 days.

(21) Appl. No.: 17/256,900

(22) PCT Filed: May 9, 2019

(86) PCT No.: PCT/CN2019/086239
§ 371 (c)(1),
(2) Date: Dec. 29, 2020

(87) PCT Pub. No.: WO2020/042664
PCT Pub. Date: Mar. 5, 2020

(65) Prior Publication Data
US 2021/0275114 A1    Sep. 9, 2021

(30) Foreign Application Priority Data
Aug. 27, 2018 (CN) .......................... 201810982519.2

(51) Int. Cl.
*A61B 6/03* (2006.01)
*G01R 29/02* (2006.01)
*G06T 11/00* (2006.01)

(52) U.S. Cl.
CPC .............. *A61B 6/037* (2013.01); *G01R 29/02* (2013.01); *G06T 11/005* (2013.01); *G06T 2207/10104* (2013.01)

(58) Field of Classification Search
CPC ....... A61B 6/037; G01R 29/02; G06T 11/005; G06T 2207/10104
See application file for complete search history.

(56) References Cited

U.S. PATENT DOCUMENTS

| 1,022,847 A | 4/1912 | Jaccard |
| 5,274,569 A | 12/1993 | Prasad |

(Continued)

FOREIGN PATENT DOCUMENTS

| CN | 102262238 A | 11/2011 |
| CN | 102789952 A | 11/2012 |

(Continued)

OTHER PUBLICATIONS

International Search Report dated Aug. 5, 2019 from counterpart International Application No. PCT/CN2019/086239, 7 pp.

(Continued)

*Primary Examiner* — Utpal D Shah
(74) *Attorney, Agent, or Firm* — Shumaker & Sieffert, P.A.

(57) ABSTRACT

The present disclosure discloses a method and device for sampling a pulse signal, and a computer program medium. The method comprises: collecting a plurality of first sampling points on a rising edge portion of the pulse signal according to a plurality of preset sampling thresholds, where each of the plurality of first sampling points is represented by one of the preset sampling thresholds and first time corresponding to the one of the preset sampling thresholds (S1); collecting a plurality of second sampling points on a falling edge portion of the pulse signal according to the (Continued)

plurality of preset sampling thresholds, where each of the second sampling points is represented by one of the preset sampling thresholds and second time corresponding to the one of the preset sampling thresholds (S2); and collecting a third sampling point of the pulse signal at third time separated from the first or second time by a preset time interval, where the third sampling point is represented by the third time and a response amplitude corresponding to the third time (S3). By using the technical solutions provided by the present disclosure, it can improve the sampling efficiency of the pulse signal and reduce energy consumption.

12 Claims, 4 Drawing Sheets

(56) References Cited

U.S. PATENT DOCUMENTS

| | | | |
|---|---|---|---|
| 9,344,102 B2* | 5/2016 | Xi | H03M 1/1057 |
| 9,772,408 B2 | 9/2017 | Xie et al. | |
| 10,120,342 B2 | 11/2018 | Xi et al. | |
| 10,228,470 B2 | 3/2019 | Wu et al. | |
| 2008/0001884 A1 | 1/2008 | Eames | |
| 2014/0052414 A1* | 2/2014 | Xie | G01T 1/2006 |
| | | | 702/189 |
| 2015/0372689 A1* | 12/2015 | Xi | H03M 1/1057 |
| | | | 341/118 |
| 2016/0291167 A1* | 10/2016 | Xie | G01T 1/208 |
| 2018/0299566 A1* | 10/2018 | Lee | G01T 1/208 |

FOREIGN PATENT DOCUMENTS

| | | |
|---|---|---|
| CN | 202801645 U | 3/2013 |
| CN | 103961126 A | 8/2014 |
| CN | 104639123 A | 5/2015 |
| CN | 105212954 A | 1/2016 |
| CN | 107024711 A | 8/2017 |
| CN | 109171787 A | 1/2019 |
| EP | 1148348 A3 | 4/2001 |
| EP | 3614181 A1 | 2/2020 |
| WO | 2013085923 A1 | 6/2013 |

OTHER PUBLICATIONS

Chinese Office Action for corresponding CN Application No. 201810982519.2, dated Dec. 4, 2019, 9 pages.
Chinese Office Action for corresponding CN Application No. 201810982519.2, dated Jul. 23, 2020, 10 pages.

* cited by examiner

METHOD AND DEVICE FOR SAMPLING A PULSE SIGNAL, AND COMPUTER PROGRAM MEDIUM

This application is a national stage application under 35 U.S.C. § 371 of PCT Application No. PCT/CN2019/086239, filed May 9, 2019, which claims the benefit of China Application No. 201810982519.2, filed Aug. 27, 2018. The entire contents of each of PCT Application No. PCT/CN2019/086239 and China Application No. 201810982519.2 are incorporated herein by reference in their entireties.

TECHNICAL FIELD

This disclosure relates to the technical field of signal processing, and in particular to a method and a device for sampling a pulse signal, and a computer program medium.

BACKGROUND

Positron Emission Tomography (abbr. PET) is a technique that uses radioactive elements for clinical imaging. The processes of this technique include: labeling the positron-emitting radionuclides into a compound that is able to be added in the blood flow or participate in the metabolic process of living tissues, and then injecting the compound labeled with the radionuclides into a subject. Positrons emitted by the radionuclides in the body moves about 1 mm and then combines with negative electrons in the subject's body to annihilate the electron pairs, and thus generate gamma photons, which can be received by the scintillation crystal and converted into visible light, which in turn are converted into pulse signals by the photoelectric converter for reconstruction, thereby helping to determine the enrichment site of the radionuclides, locate the area of vigorous metabolism and evaluate the activity of the radionuclides.

In PET or other related fields, the pulse signal needs to be sampled before the pulse signal being reconstructed. In the prior art, the time interval sampling method is commonly used for sampling. Specifically, the amplitude corresponding to each time point of the pulse signal is recorded according to an identical time interval, such that each time point and its corresponding amplitude constitute one sampling point.

SUMMARY

In the process of realizing this disclosure, the inventors found at least the following problems in the prior art:

The time interval sampling method in the prior art involves a long sampling time due to too many sampling points and too much recorded information, resulting in low sampling efficiency and high energy consumption.

In order to solve the above technical problems, a method and a device for sampling a pulse signal, and a computer program medium may be provided in the embodiments of the disclosure, which are implemented as follows:

A method for sampling a pulse signal is provided, comprising:

step S1, collecting a plurality of first sampling points on a rising edge portion of the pulse signal according to a plurality of preset sampling thresholds, where each of the first sampling points is represented by one of the preset sampling thresholds and first time corresponding to the one of the preset sampling thresholds;

step S2, collecting a plurality of second sampling points on a falling edge portion of the pulse signal according to the plurality of preset sampling thresholds, where each of the second sampling points is represented by one of the preset sampling thresholds and second time corresponding to the one of preset sampling thresholds; and step S3, collecting a third sampling point of the pulse signal at third time separated from the first or second time by a preset time interval, where the third sampling point is represented by the third time and a response amplitude corresponding to the third time.

Preferably, the step S1 comprises:

recording a quantity of the first time when an amplitude of the pulse signal reaches the plurality of preset sampling thresholds on the rising edge portion of the pulse signal to determine the plurality of first sampling points.

Preferably, the step S1 comprises:

when one of the preset sampling thresholds corresponds to a quantity of the first time, calculating the average value of the maximum time and the minimum time among the quantity of the first time, or calculating the average value of the quantity of the first time, and using the calculated average value as the first time corresponding to the one of the preset sampling thresholds.

Preferably, the preset sampling thresholds include voltage thresholds, current thresholds, or thresholds of magnetic field intensity.

Preferably, the preset sampling thresholds are set according to trigger characteristic of the pulse signal or a pre-statistical empirical value of the amplitude.

Preferably, the step S3 comprises:

collecting the third sampling point on the rising edge portion, a peak or the falling edge portion after the plurality of first sampling points of the pulse signal, at the third time separated from the first time by the preset time interval, or, collecting the third sampling point on the falling edge portion or a valley after the plurality of second sampling points of the pulse signal, at the third time separated from the second time by the preset time interval.

Preferably, the step S3 comprises:

determining, at the third time, the response amplitude of the pulse signal corresponding to the third time to determine the third sampling point.

Preferably, the preset time interval is determined in the following manners of:

calculating, for each of a plurality of pre-collected pulse signals, a difference between an abscissa value of a pulse amplitude point and an abscissa value of a selected calibration point, where the calibration point is one of the plurality of the first sampling points or one of the plurality of the second sampling points;

performing Gaussian fitting on the calculated differences to obtain Gaussian curves and fitted parameters; and comparing discrete degrees of the obtained Gaussian curves with each other, and using the fitted parameter of the Gaussian curve conforming to an optimal normal distribution as the preset time interval.

A device for sampling a pulse signal is provided, comprising:

a first sampling unit configured to collect a plurality of first sampling points on a rising edge portion of the pulse signal according to a plurality of preset sampling thresholds, where each of the first sampling points is represented by one of the preset sampling thresholds and first time corresponding to the one of the preset sampling thresholds;

a second sampling unit configured to collect a plurality of second sampling points on a falling edge portion of the pulse signal according to the plurality of preset sampling thresholds, where each of the second sampling points is represented by one of the preset sampling thresholds and second time corresponding to the one of the preset sampling thresholds; and a third sampling unit configured to collect a third sample point of the pulse signal at third time separated from the first or second time by a preset time interval, where the third sample point is represented by the third time and a response amplitude corresponding to the third time.

A computer program medium is provided, comprising:

a memory having instructions stored therein, and a processor connected to the memory and configured to execute following operations according to instructions stored in the memory:

collecting a plurality of first sampling points on a rising edge portion of the pulse signal according to a plurality of preset sampling thresholds, where each of the first sampling points is represented by one of the preset sampling thresholds and first time corresponding to the one of the preset sampling thresholds;

collecting a plurality of second sampling points on a falling edge portion of the pulse signal according to the plurality of preset sampling thresholds, where each of the second sampling points is represented by one of the preset sampling thresholds and second time corresponding to the one of the preset sampling thresholds; and collecting a third sampling point in the pulse signal at third time separated from the first or second time by a preset time interval, where the third sampling point is represented by the third time and a response amplitude corresponding to the third time.

As can be seen from the technical solutions provided by the above embodiments of the disclosure, multi-threshold sampling according to the embodiments of the disclosure is performed on the rising and falling edge portion of the pulse signal, and then the pulse signal is further sampled at a time interval in addition to the multi-threshold sampling, which will improve the sampling efficiency of the pulse signal and reduce energy consumption. In addition, by using the technical solutions provided by the embodiments of the disclosure, the amplitude variation of the pulse signal could be well captured, so that it will improve the accuracy of the subsequent reconstructed waveform of the pulse signal.

BRIEF DESCRIPTION OF THE DRAWINGS

In order to describe the technical solution in the embodiments of the disclosure or the prior art more clearly, accompanying drawings required to be used in the description of the embodiments or the prior art will be introduced briefly as follows. It is apparent that the drawings as shown are merely illustrative of some embodiments as recited in the disclosure. It should be understood by those skilled in the art that various alternatives to the drawings may be appreciated, without creative work involved.

DETAILED DESCRIPTION

The technical solutions in the embodiments of the disclosure will be clearly and comprehensively described in the following description with reference to the accompanying drawings. It is apparent that the described embodiments are only provided to illustrate some exemplary embodiments of the disclosure, rather than exhaustively elaborate all of them, which shall not be construed to limit the scope of the disclosure or the claims. It should be understood that various alternatives to the embodiments described herein may be employed by those skilled in the art without creative work involved and without departing from the scope of the disclosure.

Notably, when an element is referred to as being "disposed on" another element, it can be directly disposed on another element or there may be an intermediate element. When an element is referred to as being "connected or coupled" to another element, it may be directly connected or coupled to another element or there is an intermediate element. The term "connection or coupling" used herein may include electrical connection or coupling and/or mechanical or physical connection or coupling. The term "comprise or include" used herein refers to the existence of features, steps or elements, but does not exclude the existence or addition of one or more other features, steps or elements. The term "and/or" used herein includes any and all combinations of one or more of the related listed items. The terms "a", "an", "one", "the" and other similar terms include both singular and plural forms, unless context clearly dictates otherwise.

Unless otherwise indicated, all the technical and scientific terms used herein have general meaning as commonly understood by those skilled in the technical field related to the disclosure. The terms used herein are for the purpose of describing specific embodiments, but not intended to limit the disclosure.

In addition, the terms "first", "second", "third" or the like used herein are only for the purpose of description and to distinguish similar objects from each other, which do not express the sequence thereof, nor can they be understood as indication or implication of relative importance. In addition, in the description of this disclosure, unless otherwise specified, "a plurality/quantity of" means two or more.

A method and a device for sampling a pulse signal, and a computer program medium provided by the embodiments of the present disclosure will be described in detail below with reference to the accompanying drawings.

Figure 1:
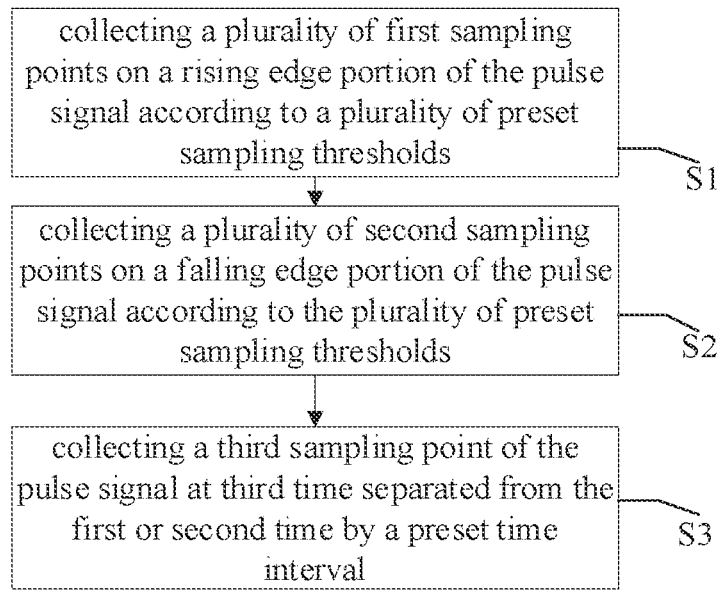
FIG. 1 is a flowchart of the method for sampling a pulse signal according to an embodiment of the present disclosure.

As shown in FIG. 1, a method for sampling a pulse signal according to an embodiment of the present disclosure is provided, which includes the following steps:

S1: collecting a plurality of first sampling points on the rising edge portion of the pulse signal according to a plurality of preset sampling thresholds.

After actively acquiring or receiving a pulse signal from a radiation detector, such as a scintillation crystal detector or a gas ionization detector, or the like, it may sample the pulse signal via multi-threshold sampling. For example, it may sequentially collect a plurality of first sampling points on the rising edge of the pulse signal according to a plurality of preset sampling thresholds. Specifically, firstly, it may record a quantity of first time when the amplitude of the pulse signal reaches a plurality of preset sampling thresholds on the rising edge portion of the pulse signal, such that the plurality of first sampling points on the rising edge portion of the pulse signal may be determined, and related information of the plurality of first sampling points, such as amplitude, time or the like, may be also recorded. Each of the first sampling points may be represented by one of the plurality of preset sampling thresholds and the first time corresponding to the preset sampling threshold. For example, the first sampling points may have coordinates represented by (Ti, Mi), where T represents time, M represents amplitude, and i is a positive integer.

On the rising edge portion of the pulse signal, if one preset sampling threshold corresponds to a quantity of first time, it may calculate the average value of the maximum time and the minimum time among the quantity of first time, or the average value of the quantity of first time, and then it may use the calculated average value as the first time corresponding to the preset sampling threshold. The first time may also be determined in other ways, without limitation applied thereto. The pulse signal may be an electric signal, such as an electric pulse signal, an optical signal, a sound signal or the like. The preset sampling threshold could be an electrical threshold, such as a voltage threshold or a current threshold, or other thresholds, such as a magnetic threshold, for example magnetic field strength. The preset sampling threshold may be set according to the characteristics of the pulse signal, for example, trigger level, pulse amplitude. Alternatively, the preset sampling threshold may be set according to the pre-statistical empirical value of the amplitude of the pulse signal. The number of the preset sampling thresholds may be selected according to actual needs, without limitation applied thereto.

S2: collecting a plurality of second sampling points on the falling edge portion of the pulse signal according to the plurality of preset sampling thresholds.

After determining, on the rising edge portion of the pulse signal, the quantity of first time corresponding to the plurality of preset sampling thresholds, it may apply multi-threshold sampling on the falling edge portion of the pulse signal in the same manner. Specifically, it may record a quantity of second time when the amplitude of the pulse signal reaches a plurality of preset sampling thresholds on the falling edge portion of the pulse signal, such that the plurality of second sampling points on the falling edge portion of the pulse signal may be determined, and related information of the plurality of second sampling points, such as amplitude, time or the like, may be also recorded. Each of the second sampling points may be represented by one of the plurality of preset sampling thresholds and second time corresponding to the preset sampling threshold.

Similarly, if one preset sampling threshold corresponds to a quantity of second time, it may calculate the average value of the maximum time and the minimum time among the quantity of second time, or the average value of the quantity of the second time, and then it may use the calculated average value as the second time corresponding to the preset sampling threshold. The second time may also be determined in other ways, without limitation applied thereto.

For the details of this step, reference may be made to the above step S1, which will not be elaborated here.

S3: collecting a third sampling point of the pulse signal at third time separated from the first or second time by a preset time interval.

After determining the multiple first time corresponding to a plurality of preset sampling thresholds on the rising edge portion of the pulse signal or the quantity of second time corresponding to a plurality of preset sampling thresholds on the falling edge portion of the pulse signal, it may further sample the pulse signal by time-sampling, in order to improve the accuracy of the sampling and help to determine the maximum amplitude point or the minimum amplitude point of the pulse signal.

In a specific embodiment, it may use any one or more first sampling points, for example, the last recorded first sampling point or other first sampling point(s) as calibration point(s), to determine, at third time separated from the first time of the calibration point(s) by the preset time interval (A), a response amplitude corresponding to the third time of the pulse signal, such that it may determine the third sampling point on the rising edge portion, a peak or the falling edge portion after the plurality of first sampling points of the pulse signal, and then it may record the related information, such as amplitude, time or the like, of the third sampling point. The third time may be the sum of the first time and the preset time interval (A).

In another specific embodiment, it may use any one or more second sampling points, for example, the third one of the second sampling points as recorded, or other second sample point(s) as the calibration point(s), to determine, at third time separated from the second time of calibration point(s) by a preset time interval (A), a response amplitude corresponding to the third time of the pulse signal, such that it may determine the third sampling point on a valley or the falling edge portion after the a plurality of second sampling points of the pulse signal. The third time may be the sum of the second time and the preset time interval (A).

Figure 3:
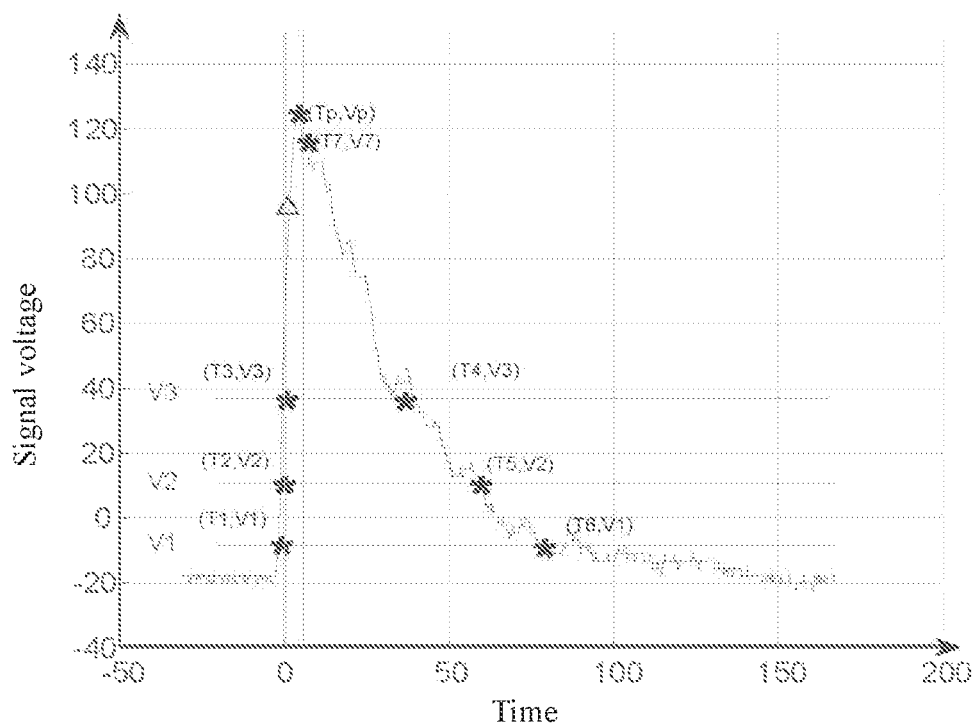
FIG. 3 is a schematic diagram of the sampling result obtained by using the sampling method in FIG. 2.

The third sampling point is preferably a pulse amplitude point, for example, a peak (for example, as shown in FIG. 3), but may also be one or more other data point(s). Each third sampling point may be represented by one third time and a response amplitude corresponding to the one third time.

The preset time interval may be set arbitrarily, or may be determined in advance through experiments, in order to improve the sampling effect. For example, when a peak is used as the third sampling point, the preset time interval may be determined in the following way, but not limited thereto:

(1) collecting a plurality of (for example, 100,000) pulse signals in advance, and recording the first sampling points on the rising edge portion of each of the pulse signals and the pulse amplitude point (i.e., the peak);

(2) calculating, for each of the plurality of pulse signals, a difference between an abscissa of the pulse amplitude point and an abscissa of a selected calibration point, respectively, where the calibration point is one of the first sampling points;

(3) performing Gaussian fitting, of which the specific process may refer to the prior art, on the plurality of calculated differences to obtain Gaussian curves and fitted parameters; and (4) comparing discrete degrees of the obtained Gaussian curves with each other, and using the fitted parameter corresponding to the Gaussian curve conforming to an optimal normal distribution as the preset time interval.

Similarly, the valley may also be used as the third sampling point, and the preset time interval may be determined in the manners as mentioned above, while in this case, the calibration point is one of the plurality of second sampling points.

It should be noted that the above steps S1 to S3 do not necessarily need to be executed strictly in the above order. The steps S3 and S1 may also be executed in an alternative manner. For example, after collecting first one of the first sampling points in the step S1, it may execute the step S3. In addition, for the case where the third time is separated from the first time by a preset time interval, the step S3 may be executed before the step S2, or could be executed in an alternative manner as to the step S2.

The plurality of first sampling points, the plurality of second sampling points, and the third sampling point as collected constitute all sampling points of the pulse signal. By recording the relevant information of the sampling points, it may obtain the characteristic information of the pulse signal, such as the amplitude, the rising slope, the rising time, the falling time and the like, which may provide a basis for subsequent classification and fitting for the pulse signal.

In the followings, the execution process of the above steps will be embodied in an example where the voltage thresholds are used as the preset sampling thresholds and there are 9 sampling points to be collected.

Figure 2:
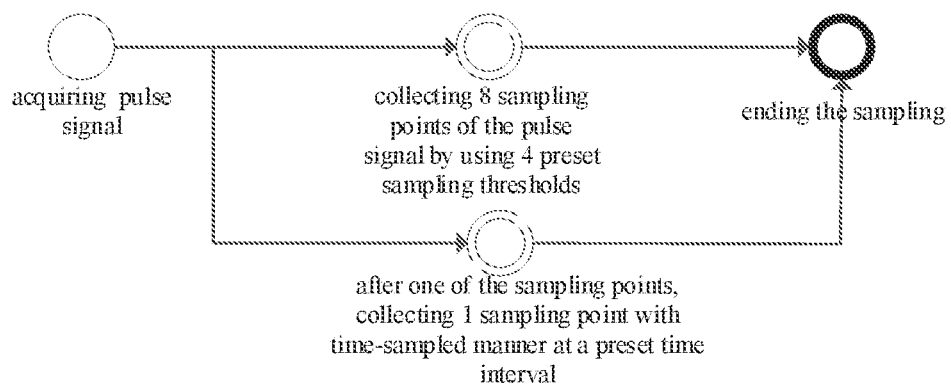
FIG. 2 is a specific operation flowchart of the sampling method according to FIG. 1.

As shown in FIG. 2, sampling is performed based on the voltage thresholds, in which four preset voltage thresholds (V1, V2, V3, V4) may be used to determine the corresponding first time (T1, T2, T3, T4) on the rising edge portion of the pulse signal, thereby obtaining four first sampling points (T1, V1), (T2, V2), (T3, V3) and (T4, V4), and to determine the corresponding second time (T5, T6, T7, T8) on the falling edge portion of the pulse signal, thereby obtaining four second sampling points (T5, V4), (T6, V3), (T7, V2) and (T8, V1). The sampling is performed at a time interval, in which the third sampling point (T9, V9) may be sampled at a preset time interval after the fourth of the first sampling points. The above 9 sampling points constitute all the sampling points of the pulse signal. In FIG. 3, there are 3 preset voltage thresholds (V1, V2, V3) and 7 sample points (T1, V1), (T2, V2), (T3, V3), (T4, V3), (T5, V2), (T6, V1) and (T7, V7) as well as the peak (Tp, Vp), as illustrated.

It can be seen from the above description that in the embodiments of the present disclosure, by performing multi-threshold sampling on the rising edge and falling edge portion of the pulse signal, and by sampling the pulse signal at a time interval in addition to the multi-threshold sampling, the sampling efficiency can be improved while the energy consumption of the hardware can be reduced, such that the costs can also be reduced. A basis for subsequent classification of the sampling points can be provided as well. In addition, sampling the pulse signal at a time interval in addition to the multi-threshold sampling may retain more information from the original pulse signal, thereby reducing the difficulty of subsequent reconstruction of the pulse signal and improving the precision of subsequent reconstruction of the pulse signal. In addition, by using the technical solutions provided in the embodiments of the present disclosure, it may well capture the amplitude variation of the pulse signal, such that the accuracy of the subsequently reconstructed waveform of the pulse signal may be improved.

The beneficial effects in the embodiments of the present disclosure will be illustrated with specific examples as follows.

Figure 4:
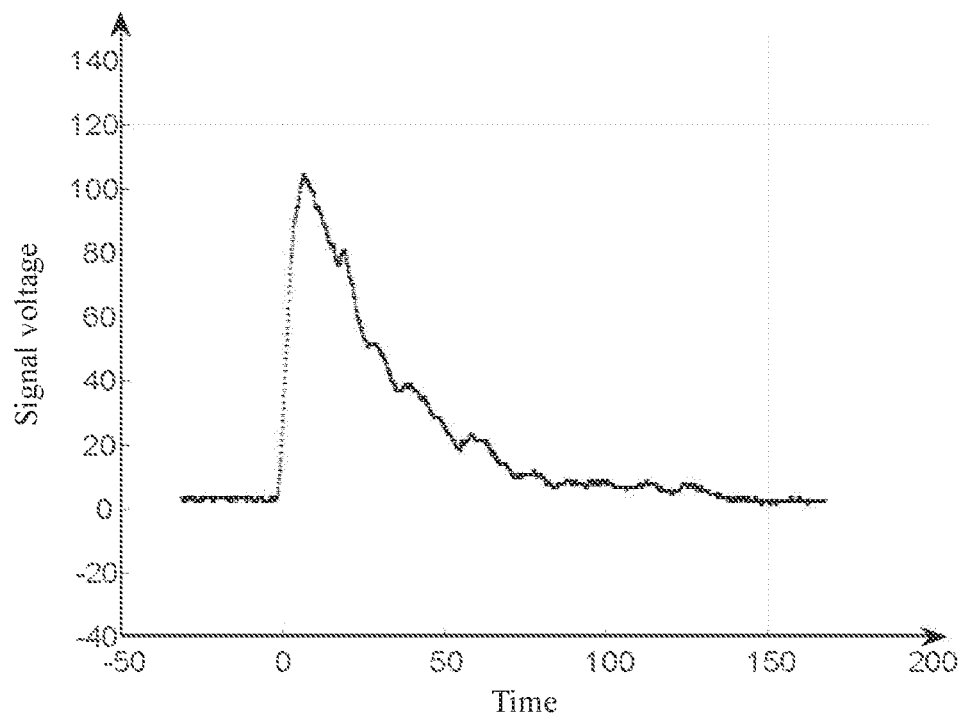
FIG. 4 is a schematic diagram of the result of sampling a pulse signal by using a time interval sampling method in the prior art.
Figure 5:
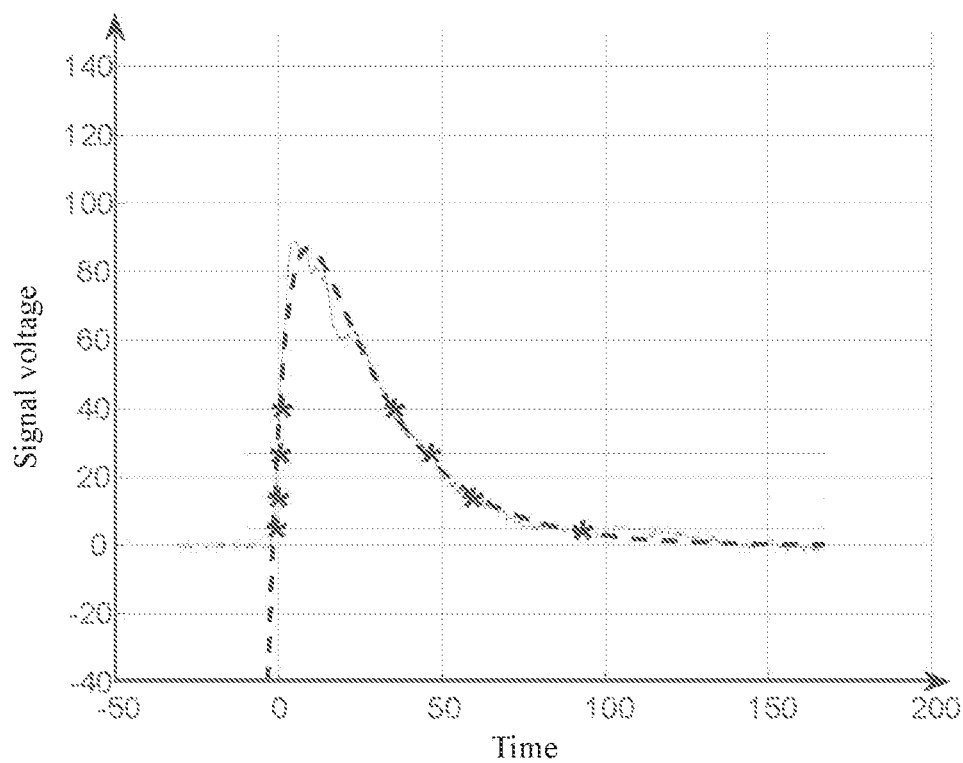
FIG. 5 is a schematic diagram of the comparison between the fitted curve obtained by fitting a pulse signal after performing multi-threshold sampling on the pulse signal and an actual measured curve in the prior art.
Figure 6:
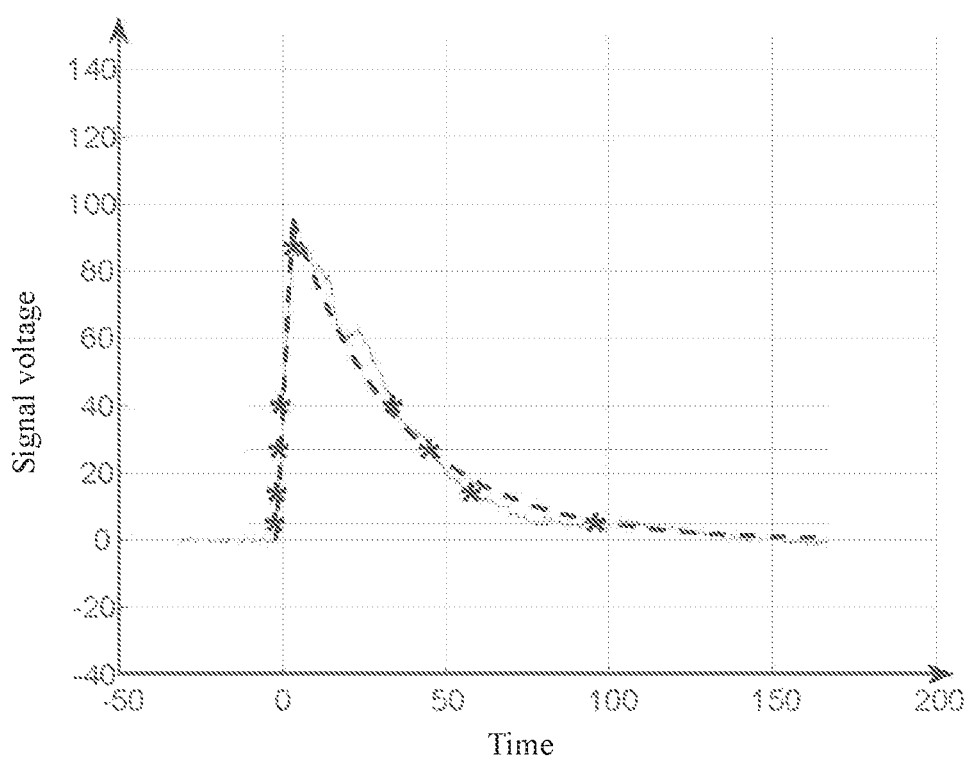
FIG. 6 is a schematic diagram of the comparison between the fitted curve obtained by fitting a pulse signal after sampling the pulse signal using the sampling method provided in an embodiment of the present disclosure and an actual measured curve.

FIG. 4 is a schematic diagram of the result of sampling a pulse signal at a time interval in the prior art. FIG. 5 is a schematic diagram of comparison between the fitted curve obtained by fitting a pulse signal after performing multi-threshold sampling on the pulse signal and the actual measured curve in the prior art. FIG. 6 is a schematic diagram of the comparison between the fitted curve obtained by fitting a pulse signal after sampling the pulse signal using the sampling method provided by the embodiments of the present disclosure and the actual measured curve. Wherein, the solid line represents the actual measured curve, the dashed line represents the fitted curve, and the fitting methods used in FIGS. 5 and 6 are the same.

By comparing FIG. 4 with FIG. 6, it can be seen that for sampling the same pulse signal in the same time period, the number of sampling points required by the sampling method provided in the embodiments of the present disclosure is far less than the number of sampling points required by the time interval sampling method in the prior art. By using the sampling method provided by the embodiments of the disclosure, it only requires collecting several (for example, 9) sampling points, while by using the time interval sampling method in the prior art, it requires collecting at least hundreds of sampling points, or even thousands of sampling points. It can be seen that, by using the sampling method provided by the embodiments of the present disclosure, it could reduce the number of sampling points as required, thereby improving the sampling efficiency and reducing the cost.

By comparing FIG. 5 with FIG. 6, it can be seen that compared with the multi-threshold sampling method in the prior art, by using the sampling method provided by the embodiments of the present disclosure, it can make the fitted curve obtained by subsequent fitting process closer to the actual measured curve. It can be seen that both the accuracy of the subsequently reconstructed waveform of the pulse signal and the precision of the subsequent reconstruction of the signal could be improved by using the sampling method provided in the embodiments of the present disclosure.

Figure 7:
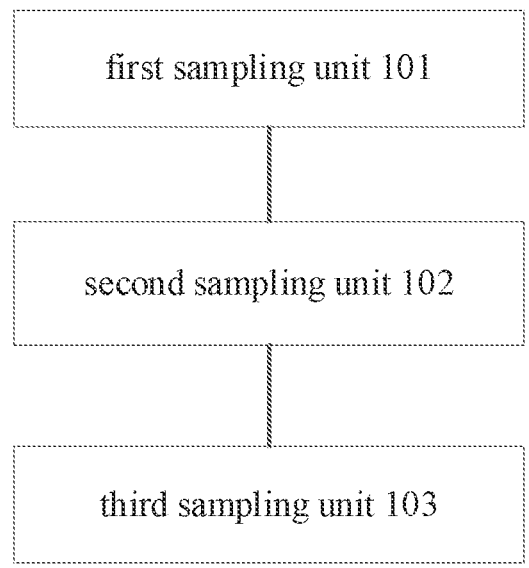
FIG. 7 is a schematic structural diagram of a device for sampling a pulse signal according to an embodiment of the present disclosure.

In the embodiments of the present disclosure, a device for sampling a pulse signal is provided, as shown in FIG. 7. The sampling device may include:

a first sampling unit 101, which may be configured to collect a plurality of first sampling points on the rising edge portion of the pulse signal according to a plurality of preset sampling thresholds, where each of the first sampling points is represented by one of the plurality of the preset sampling thresholds and first time corresponding to the preset sampling threshold;

a second sampling unit 102, which may be configured to collect a plurality of second sampling points on the falling edge portion of the pulse signal according to the plurality of preset sampling thresholds, where each of the second sampling points is represented by one of the plurality of the preset sampling thresholds and second time corresponding to the preset sampling threshold; and a third sampling unit 103, which may be configured to collect a third sampling point of the pulse signal at third time separated from the first or second time by a preset time interval, with the third sampling point is represented by the third time and a response amplitude corresponding to the third time.

After actively acquiring or receiving a pulse signal from a radiation detector such as a scintillation crystal detector or a gas ionization detector, the first sampling unit 101 may record a quantity of the first time when the amplitude of the pulse signal reaches the plurality of preset sampling thresholds on the rising edge portion of the pulse signal, such that it may determine the plurality of the first sampling points on the rising edge portion of the pulse signal, and thus record related information of the plurality of the first sampling points. After collecting the first sampling points by the first sampling unit 101, the second sampling unit 102 may record a quantity of second time when the amplitude of the pulse signal reaches the plurality of preset sampling thresholds on the falling edge portion of the pulse signal, such that it may determine a plurality of the second sampling points on the falling edge portion of the pulse signal, and thus record related information of the plurality of the second sampling points. The third sampling unit 103 may also determine, at third time separated from the first or second time by a preset time interval, the response amplitude corresponding to the third time of the pulse signal, so as to determine the third sampling point of the pulse signal, and record the relevant information of the third sampling point.

For the detailed description of the embodiment, reference can be made to the sampling method in FIG. 1, which will not be elaborated here.

It may perform, by using the above-mentioned device, multi-threshold sampling on the rising and falling edge portions of the pulse signal, and sample the pulse signal at a time interval based on the multi-threshold sampling, which can improve sampling efficiency, reduce energy consumption of hardware, and thus reduce costs, and can also provide a basis for subsequent classification of the sampling points. In addition, sampling the pulse signal at time intervals based on the multi-threshold sampling can retain more information of the original pulse signal, thereby reducing the difficulty of subsequent reconstruction of the pulse signal, and also improving the precision of subsequent reconstruction of the pulse signal. In addition, by using the technical solutions provided in the embodiments of the present disclosure, it may well capture the amplitude changes of the pulse signal, so as to improve the accuracy of the subsequently reconstructed waveform of the pulse signal.

Figure 8:
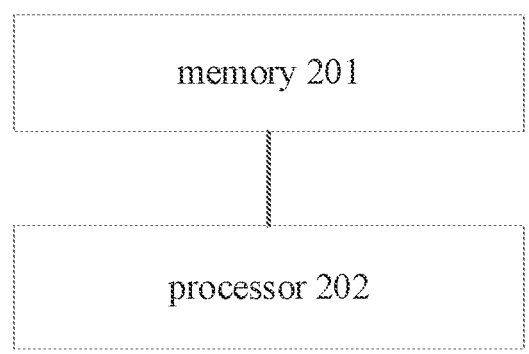
FIG. 8 is a schematic structural diagram of a computer program medium according to an embodiment of the present disclosure.

The embodiments of the present disclosure also provide a computer program medium for sampling pulse signals, as shown in FIG. 8. The computer program medium can include:
- a memory 201 having instructions stored therein, and
- a processor 202, which is coupled to the memory 201 and may be configured to execute the following operations according to the instructions stored in the memory 201:
  collecting a plurality of first sampling points on the rising edge portion of the pulse signal according to a plurality of preset sampling thresholds, where each of the plurality of first sampling points is represented by one of the plurality of preset sampling thresholds and the first time corresponding to the preset sampling threshold;
  collecting a plurality of second sampling points on the falling edge portion of the pulse signal according to the plurality of preset sampling thresholds, where each of the plurality of second sampling point is represented by one of the plurality of preset sampling thresholds and the second time corresponding to the preset sampling threshold; and
  collecting a third sampling point of the pulse signal at third time separated from the first or second time by a preset time interval, where the third sample point is represented by the third time and the response amplitude corresponding to the third time.

For the detailed description of this embodiment, reference can be made to the sampling method in FIG. 1, which will not be elaborated here.

It should be noted that the foregoing sampling method, device, and computer program medium provided in the embodiments of the present disclosure are not limited to being applied to the fields of PET, Multi-Voltage Threshold (MVT) or the like, and may also be applied to any field that needs to sample pulse signals.

The devices, units or the like described in the above embodiments may be specifically implemented by computer chips and/or entities, or implemented by products with specific functions. For the convenient purpose, description is made respectively of different functional units of the devices. Of course, when implementing the disclosure, the functions of the individual units may be embodied in the same one or more computer chips.

Although the method steps described in the above-mentioned embodiments or flowcharts are provided in the disclosure, more or fewer steps may be included in the methods with conventional or routine work. The execution order of the steps, in which there is no necessary causal relationship logically, is not limited to that provided in the embodiments in the disclosure.

The various embodiments in this specification are described in a progressive manner with the same or similar parts to be referred across the various embodiments, while the description of each embodiment focus on the differences from other embodiments.

The above-mentioned embodiments are described to facilitate those skilled in the art to understand and practice the disclosure. It is also apparent to those skilled in the art to make various modifications to these embodiments and apply the general principles described herein to other embodiments without creative work. Therefore, this disclosure is not limited to the above-mentioned embodiments, and improvements and modifications made by those skilled in the art based on this disclosure without departing from the scope of this disclosure should all fall within the protection scope of this disclosure.

What is claimed is:

1. A method for sampling a pulse signal, the method comprising:
    collecting, by a device, a plurality of first sampling points on a rising edge portion of the pulse signal according to a plurality of preset sampling thresholds, wherein each sampling point of the plurality of first sampling points is represented by one of the preset sampling thresholds and a first time corresponding to the one of the preset sampling thresholds;
    collecting, by the device, a plurality of second sampling points on a falling edge portion of the pulse signal according to the plurality of preset sampling thresholds, wherein each sampling point of the plurality of second sampling points is represented by one of the preset sampling thresholds and a second time corresponding to the one of the preset sampling thresholds; and
    collecting, by the device, a third sampling point of the pulse signal at a third time separated from the first time or the second time by a preset time interval, wherein the third sampling point is represented by the third time and a response amplitude corresponding to the third time.

2. The method according to claim 1, wherein collecting the plurality of first sampling points on the rising edge portion of the pulse signal comprises:
recording a corresponding quantity of the first time when an amplitude of the pulse signal reaches each of the plurality of preset sampling thresholds on the rising edge portion of the pulse signal to determine the plurality of first sampling points.

3. The method according to claim 1, wherein collecting the plurality of first sampling points on the rising edge portion of the pulse signal comprises:
when one of the preset sampling thresholds corresponds to a corresponding quantity of the first time, calculating an average value of a maximum time and a minimum time among the quantity of the first time, and
using the calculated average value as the first time corresponding to the one of the preset sampling thresholds.

4. The method according to claim 1, wherein each of the plurality of preset sampling thresholds includes voltage thresholds, current thresholds, or thresholds of magnetic field intensity.

5. The method according to claim 1, wherein each of the plurality of preset sampling thresholds is set according to a trigger characteristic of the pulse signal or a pre-statistical empirical amplitude value of the pulse signal.

6. The method according to claim 1, wherein collecting the third sampling point of the pulse signal at the third time comprises:
collecting, at the third time separated from the first time by the preset time interval, the third sampling point on the rising edge portion, a peak, or the falling edge portion after the plurality of first sampling points of the pulse signal.

7. The method according to claim 1, wherein collecting the third sampling point of the pulse signal at the third time comprises:
determining, at the third time, the response amplitude of the pulse signal corresponding to the third time to determine the third sampling point.

8. The method according to claim 1, further comprising:
calculating, by the device and for each of a plurality of pre-collected pulse signals, a respective difference between an abscissa value of a pulse amplitude point and an abscissa value of a selected calibration point, where the calibration point is one of the plurality of the first sampling points or one of the plurality of the second sampling points;
performing, by the device, Gaussian fitting on calculated differences to obtain Gaussian curves and fitted parameters; and
comparing, by the device, discrete degrees of the obtained Gaussian curves with each other, and using a fitted parameter of a Gaussian curve conforming to an optimal normal distribution as the preset time interval.

9. A device for sampling a pulse signal, the device comprising:
a first sampling unit configured to collect a plurality of first sampling points on a rising edge portion of the pulse signal according to a plurality of preset sampling thresholds, wherein each sampling point of the plurality of the first sampling points is represented by one of the preset sampling thresholds and a first time corresponding to the one of the preset sampling thresholds;
a second sampling unit configured to collect a plurality of second sampling points on a falling edge portion of the pulse signal according to the plurality of preset sampling thresholds, wherein each sampling point of the second sampling points is represented by one of the preset sampling thresholds and a second time corresponding to the one of the preset sampling thresholds; and
a third sampling unit configured to collect a third sampling point of the pulse signal at a third time separated from the first time or the second time by a preset time interval, wherein the third sampling point is represented by the third time and a response amplitude corresponding to the third time.

10. A computer program medium comprising:
a memory having instructions stored therein, and
a processor connected to the memory and configured to execute following operations according to instructions stored in the memory:
collecting a plurality of first sampling points on a rising edge portion of the pulse signal according to a plurality of preset sampling thresholds, wherein each sampling point of a plurality of first sampling points is represented by one of the preset sampling thresholds and a first time corresponding to the one of the preset sampling thresholds;
collecting a plurality of second sampling points on a falling edge portion of the pulse signal according to the plurality of preset sampling thresholds, wherein each sampling point of the second sampling points is represented by one of the preset sampling thresholds and a second time corresponding to the one of the preset sampling thresholds; and
collecting a third sampling point of the pulse signal at a third time separated from the first time or the second time by a preset time interval, wherein the third sampling point is represented by the third time and a response amplitude corresponding to the third time.

11. The method according to claim 1, wherein collecting the plurality of first sampling points on the rising edge portion of the pulse signal comprises:
when one of the preset sampling thresholds corresponds to a corresponding quantity of the first time, calculating an average value of the corresponding quantity of the first time, and
using the calculated average value as the first time corresponding to the one of the preset sampling thresholds.

12. The method according to claim 1, wherein collecting the third sampling point of the pulse signal at the third time comprises:
collecting, at the third time separated from the second time by the preset time interval, the third sampling point on the falling edge portion or a valley after the plurality of second sampling points of the pulse signal.

* * * * *